(12) United States Patent
Tsukagoshi

(10) Patent No.: US 8,126,109 B2
(45) Date of Patent: Feb. 28, 2012

(54) X-RAY CT APPARATUS AND TOMOGRAPHY METHOD

(75) Inventor: Shinsuke Tsukagoshi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 399 days.

(21) Appl. No.: 12/360,911

(22) Filed: Jan. 28, 2009

(65) Prior Publication Data

US 2009/0202035 A1    Aug. 13, 2009

(30) Foreign Application Priority Data

Feb. 7, 2008   (JP) ................................. 2008-028028

(51) Int. Cl.
*A61B 6/00* (2006.01)
(52) U.S. Cl. .............................................. 378/8; 378/51
(58) Field of Classification Search .................. 378/8, 51
See application file for complete search history.

(56) References Cited

U.S. PATENT DOCUMENTS

| | | | | |
|---|---|---|---|---|
| 5,459,769 A | * | 10/1995 | Brown | 378/4 |
| 5,612,985 A | * | 3/1997 | Toki et al. | 378/4 |
| 6,289,075 B1 | * | 9/2001 | Marume | 378/8 |
| 6,337,992 B1 | | 1/2002 | Gelman | |
| 2003/0108149 A1 | | 6/2003 | Tsuyuki | |
| 2003/0161435 A1 | | 8/2003 | Ozaki | |
| 2004/0114706 A1 | | 6/2004 | Ikeda et al. | |
| 2007/0195932 A1 | * | 8/2007 | Nakaura et al. | 378/98.12 |
| 2008/0095307 A1 | * | 4/2008 | Ishida et al. | 378/15 |
| 2010/0292570 A1 | * | 11/2010 | Tsukagoshi | 600/431 |

FOREIGN PATENT DOCUMENTS

| | | |
|---|---|---|
| EP | 1 712 181 A2 | 10/2006 |
| EP | 1 769 743 A1 | 4/2007 |
| JP | 2001-508326 | 6/2001 |
| JP | 2007-275360 | 10/2007 |

* cited by examiner

*Primary Examiner* — Hoon Song
*Assistant Examiner* — Mona M Sanei
(74) *Attorney, Agent, or Firm* — Oblon, Spivak, McClelland, Maier & Neustadt, L.L.P.

(57) ABSTRACT

An index-value detecting unit detects an index value that indicates a contrast medium density in a Region Of Interest (ROI) set on an image reconstructed during a scan. A switch-timing detecting unit detects an inflection point appearing on a curve that indicates temporal variations in the contrast medium density in the ROI, based on an index value detected by the index-value detecting unit. An imaging control unit then performs control so as to skip the rest of a scanning plan in execution and to start the next scanning plan when the switch-timing detecting unit detects an inflection point.

28 Claims, 10 Drawing Sheets

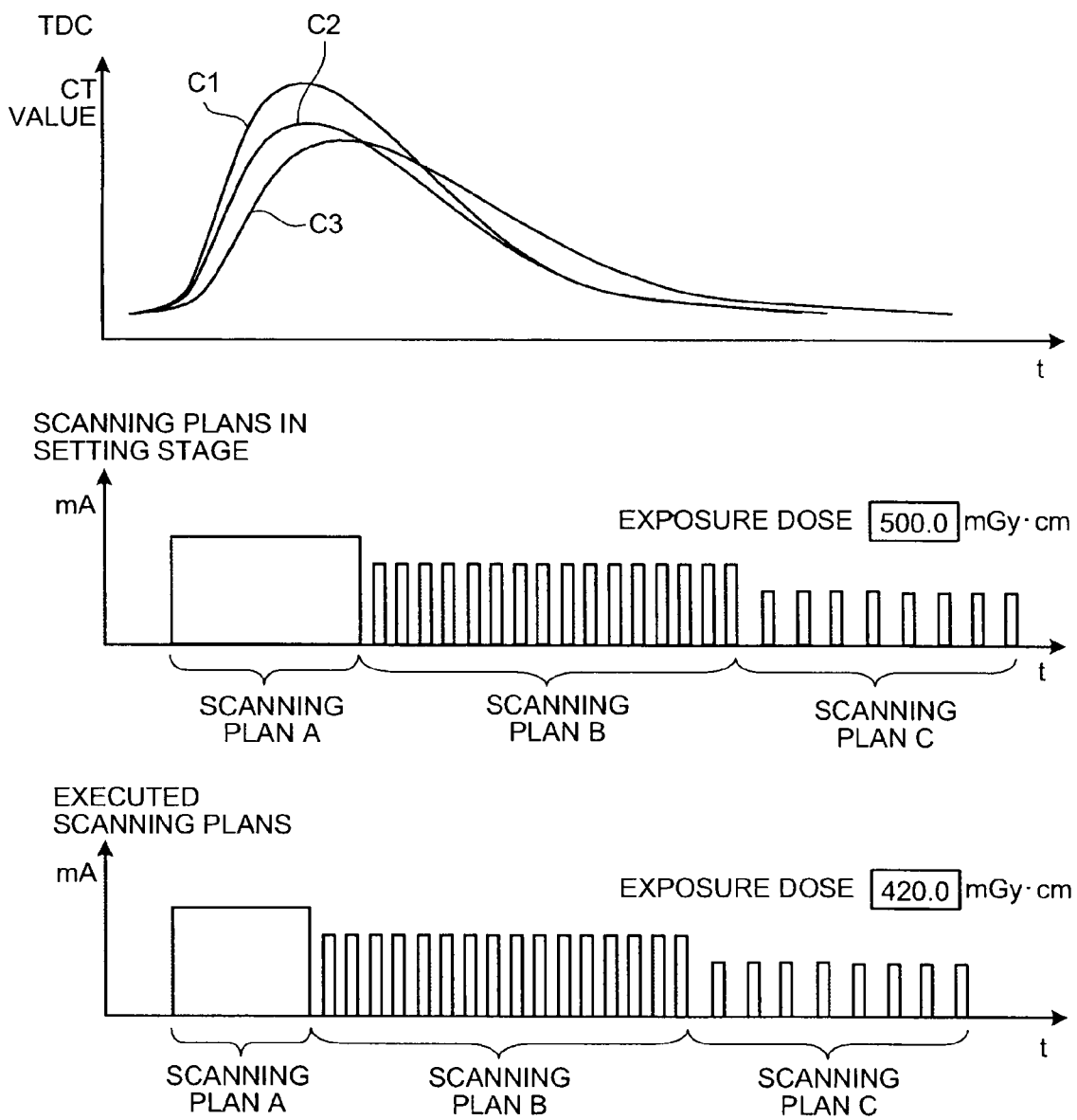

X-RAY CT APPARATUS AND TOMOGRAPHY METHOD

CROSS-REFERENCE TO RELATED APPLICATIONS

This application is based upon and claims the benefit of priority from the prior Japanese Patent Application No. 2008-28028, filed on Feb. 7, 2008; the entire contents of which are incorporated herein by reference.

BACKGROUND OF THE INVENTION

1. Field of the Invention

The present invention relates to an X-ray Computed Tomography (CT) apparatus and a tomography method for reconstructing an image by irradiating a subject, switching scanning conditions, with X-rays continuously or intermittently based on a plurality of sequential scanning plans and detecting X-rays that has passed through the subject. Particularly, the present invention relates to an X-ray CT apparatus and a tomography method by which a scan can be performed with an X-ray dose optimal for each subject.

2. Description of the Related Art

Recently, along with prevalence of an X-ray detector of multiple arrays, an X-ray CT apparatus that can take a four-dimensional image that one temporal dimension is added to three spatial dimensions has been developed. With such X-ray CT apparatus, motions of an organ or blood flow dynamics can be observed temporally, therefore, the X-ray CT apparatus can be used when performing a perfusion examination of an orthopedic region or various organs for a functional diagnosis, as well as a conventional examination for shape diagnosis.

Usually, an ordinary X-ray CT apparatus performs a scan after an operator preliminarily sets a plurality of scanning plans including various scanning conditions (for example, X-ray irradiation intervals, a scan time, and a tube current to be supplied to an X-ray tube). When taking an image for the perfusion analysis, to reduce an exposure dose to a subject, it is desirable that scanning plans are set in varying X-ray irradiation intervals in accordance with the density of a contrast medium in blood flow rather than performing a scan with regular intervals through to the end, so that scanning plans with different irradiation intervals are used in combination.

For example, when taking an image for a perfusion analysis for 60 seconds, a method of performing a continuous scan for 60 seconds may be available; however, from an exposure-dose point of view, a scan is performed by combining two or three scanning plans. Specifically, scanning plans are set as follows: because detailed data is required from the start of a scan to a peak of the density of a contrast medium, a continuous scan or an intermittent scan with short intervals is performed; a moderately intermittent scan with slightly longer intervals (for example, two-second intervals) is then performed in the middle stage during which the density of the contrast medium gradually decreases after the peak; and then an intermittent scan with much longer intervals (for example, three-second intervals) is performed in the final stage during which almost no change is observed in the contrast medium.

In this way, the conventional X-ray CT apparatus performs a scan by setting scanning plans based on a prediction of temporal variations in the density of a contrast medium. However, speeds of the circulation of a contrast medium through a body vary from subject to subject, therefore, a scan time of each scanning plan has no other choice but to be set rather long in order to perform a scan without missing a period during which the density of the contrast medium changes markedly. As a result, a subject may be sometimes irradiated with unnecessary X-rays for the perfusion analysis in some cases, for example, due to a continuous scan or an intermittent scan with short intervals that is continued even after the density of the contrast medium has peaked out in practice, or due to an intermittent scan with medium intervals that is continued despite that change in the contrast medium is hardly observed.

For this reason, it is required to perform a scan with a dose optimal for each subject by controlling the start/end of scanning plans automatically in accordance with the density of the contrast medium during the scan. As a technology of determining start timing of a scan in accordance with the density of a contrast medium, a technology is invented such that before a scan for taking an image for diagnosis (main scan), a preparatory scan (prep scan, also called "Real Prep" or "Sure Start") is performed, and then start timing of a main scan is controlled based on a temporal variation curve of CT values measured through the prep scan (for example, see JP-A 2007-275360 (KOKAI)).

However, according to the conventional technology represented by JP-A 2007-275360 (KOKAI), even though start timing of a main scan can be controlled; after the main scan is started, i.e., during the scan, the start/end of a scanning plan cannot be automatically controlled in accordance with the density of the contrast medium.

SUMMARY OF THE INVENTION

According to one aspect of the present invention, an X-ray CT apparatus includes an imaging unit that irradiates a subject, switching scanning conditions, with X-rays continuously or intermittently, and reconstructs an image by detecting X-rays passed through the subject; an index-value detecting unit that detects an index value that indicates a contrast medium density in an image reconstructed by the imaging unit during a scan; a switch-timing detecting unit that detects switch timing of the scanning conditions based on an index value detected by the index-value detecting unit; and an imaging control unit that controls the imaging unit so as to skip the rest of a scan with a first scanning condition in execution and to start a scan with a second scanning condition upon detecting switch timing of the scanning conditions by the switch-timing detecting unit.

According to another aspect of the present invention, an X-ray CT apparatus includes an imaging unit that irradiates a subject, switching scanning conditions, with X-rays continuously or intermittently, and reconstructs an image by detecting X-rays passed through the subject; an index-value detecting unit that detects an index value that indicates a contrast medium density in an image reconstructed by the imaging unit during a scan; and a display control unit that displays during a scan a curve that indicates temporal variations in the contrast medium density based on index values detected by the index-value detecting unit.

According to still another aspect of the present invention, a tomography method includes irradiating a subject, switching scanning conditions, with X-rays continuously or intermittently, and reconstructing an image by detecting X-rays passed through the subject, by an imaging unit; detecting by an index-value detecting unit an index value that indicates a contrast medium density in an image reconstructed by the imaging unit during a scan; detecting by a switch-timing detecting unit switch timing of the scanning conditions based on an index value detected by the index-value detecting unit; and controlling the imaging unit by an imaging control unit so as to skip the rest of a scan with a first scanning condition in execution and to start a scan with a second scanning condition upon detecting switch timing of the scanning conditions by the switch-timing detecting unit.

According to still another aspect of the present invention, a tomography method includes irradiating a subject, switching scanning conditions, with X-rays continuously or intermittently, and reconstructing an image by detecting X-rays passed through the subject, by an imaging unit; detecting by an index-value detecting unit an index value that indicates a contrast medium density in an image reconstructed by the imaging unit during a scan; and displaying by a display control unit during a scan a curve that indicates temporal variations in the contrast medium density based on index values detected by the index-value detecting unit.

BRIEF DESCRIPTION OF THE DRAWINGS

FIG. 10 is a schematic diagram for explaining a case of displaying a plurality of curves according to the second embodiment.

DETAILED DESCRIPTION OF THE INVENTION

Exemplary embodiments of an X-ray Computed Tomography (CT) apparatus and a tomography method according to the present invention will be explained below in detail with reference to the accompanying drawings. The following description explains a case where the present invention is applied to an X-ray CT apparatus that can take a four-dimensional image that one temporal dimension is added to three spatial dimensions. A segment of a scan which is performed with a certain scanning condition is hereinafter referred to as a "scanning plan".

Figure 1:
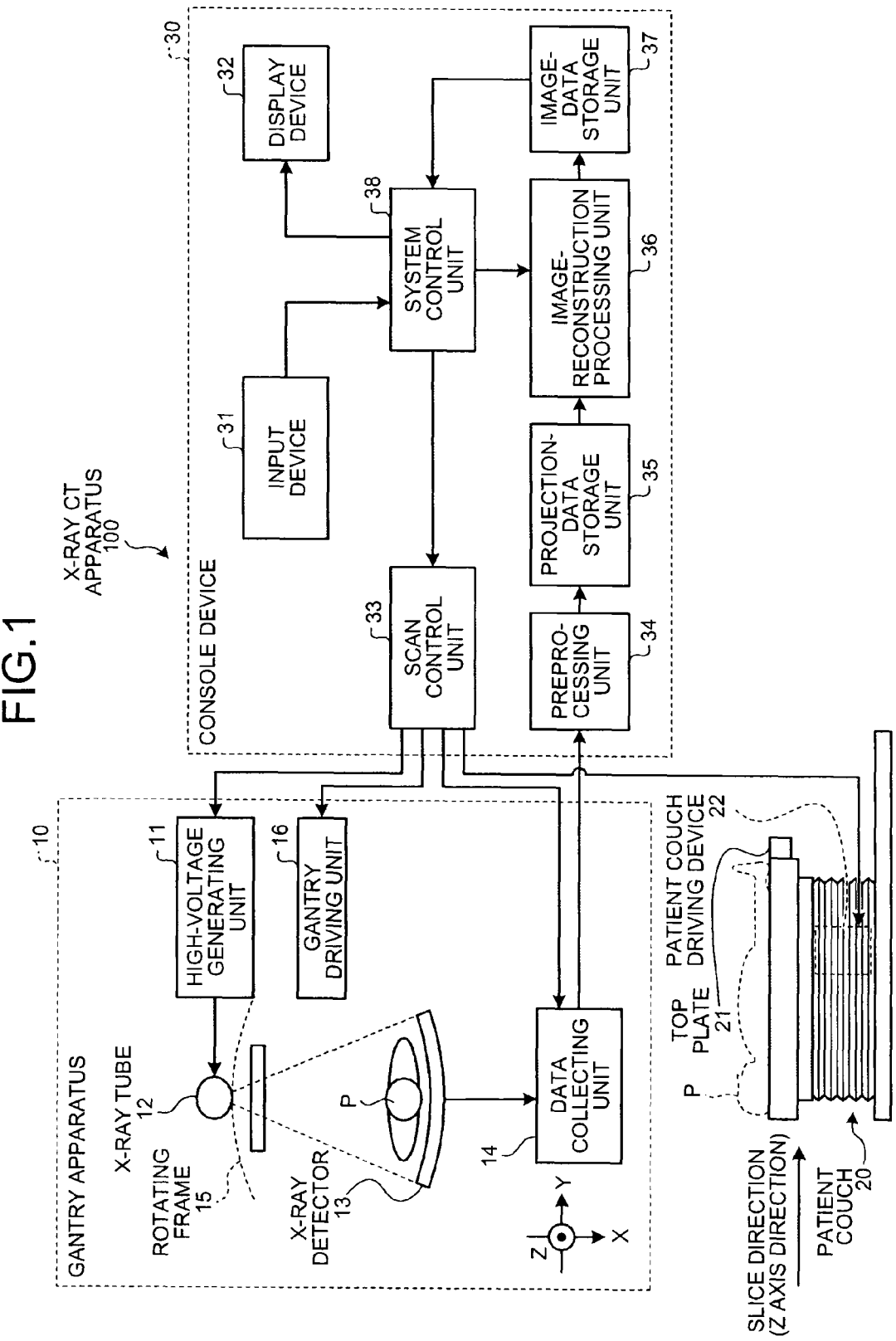
FIG. 1 is a block diagram of a general configuration of an X-ray Computed Tomography (CT) apparatus according to a first embodiment of the present invention.

First of all, a general configuration of an X-ray CT apparatus according to a first embodiment of the present invention is explained below. FIG. 1 is a block diagram of a general configuration of the X-ray Computed Tomography (CT) apparatus according to the first embodiment. As shown in FIG. 1, an X-ray CT apparatus 100 according to the first embodiment includes a gantry apparatus 10, a patient couch 20, and a console device 30.

The gantry apparatus 10 irradiates a subject P with X-rays and then collects projection data. The gantry apparatus 10 includes a high-voltage generating unit 11, an X-ray tube 12, an X-ray detector 13, a data collecting unit 14, a rotating frame 15, and a gantry driving unit 16.

The high-voltage generating unit 11 supplies a high voltage to the X-ray tube 12. The X-ray tube 12 generates X-rays with a high voltage supplied by the high-voltage generating unit 11.

The X-ray detector 13 detects X-rays that have passed through the subject P. Specifically, the X-ray detector 13 is a Flat Panel Detector (FPD) of multiple arrays that is configured by arranging detecting element arrays including a plurality of channels of X-ray sensors in a slice direction (the z axis direction shown in FIG. 1) in a plurality of rows (for example, 320 rows). The X-ray detector 13 can simultaneously detect X-rays that have passed through the subject P across a wide region, for example, a region including a scan subject portion, such as a heart or a brain.

The data collecting unit 14 creates projection data by using X-rays detected by the X-ray detector 13.

The rotating frame 15 is formed in a toroidal shape, and rotates rapidly and continuously. The rotating frame 15 supports the X-ray tube 12 and the X-ray detector 13 on opposite sides of the subject P. The gantry driving unit 16 rotates the X-ray tube 12 and the X-ray detector 13 in a circular orbit of which center is the subject P by rotationally driving the rotating frame 15.

The patient couch 20 is an equipment on which the subject P is to be placed, and includes a top plate 21 and a patient couch driving device 22. The top plate 21 is a plate on which the subject P is to be placed during a scan. The patient couch driving device 22 moves the top plate 21 to a slice direction.

The console device 30 receives various instructions related to operation of the X-ray CT apparatus 100 from an operator, and reconstructs an image from projection data collected via the gantry apparatus 10. The console device 30 includes an input device 31, a display device 32, a scan control unit 33, a preprocessing unit 34, a projection-data storage unit 35, an image-reconstruction processing unit 36, an image-data storage unit 37, and a system control unit 38.

The input device 31 includes a mouse and a keyboard, and receives an instruction to the X-ray CT apparatus 100 from the operator. For example, before a scan, the input device 31 receives setting of a plurality of sequential scanning plans, and receives setting of a Region Of Interest (ROI) on a scanned image. On the other hand, during the scan, the input device 31 receives, for example, an instruction to skip the rest of a scanning plan in execution and to start the next scanning plan. Each of the scanning plans set by the operator includes, for example, X-ray irradiation intervals, a scanning time, a tube current to be supplied to the X-ray tube.

The display device 32 includes a display device, such as a Liquid Crystal Display (LCD), and displays thereon various information. For example, the display device 32 displays thereon image data stored by the image-data storage unit 37, which will be described later, and a Graphical User Interface (GUI) for receiving various instructions from the operator.

Under the control of the system control unit 38, which will be described later, the scan control unit 33 irradiates the heart of the subject P with X-rays and collects projection data by activating the high-voltage generating unit 11, the data collecting unit 14, the gantry driving unit 16, and the patient couch driving device 22 based on scanning conditions instructed by the system control unit 38.

The preprocessing unit 34 performs preprocessing, such as sensitivity correction, on projection data created by the data collecting unit 14. The projection-data storage unit 35 stores therein projection data preprocessed by the preprocessing unit 34. The image-reconstruction processing unit 36 reconstructs an image data from projection data stored by the projection-data storage unit 35 under the control of the system control unit 38. The image-data storage unit 37 stores therein an image data reconstructed by the image-reconstruction processing unit 36.

The system control unit 38 performs overall control of the X-ray CT apparatus 100 by controlling operation of the gantry apparatus 10, the patient couch 20, and the console device 30. The system control unit 38 controls each of the units so that the subject is irradiated with X-rays continuously or intermittently based on the sequential scanning plans, and an image is reconstructed by detecting X-rays that have passed through the subject.

The general configuration of the X-ray CT apparatus 100 according to the first embodiment is explained above. According to the X-ray CT apparatus 100 of the first embodiment, a configuration and a process procedure of the system control unit 38, which performs overall control of the X-ray CT apparatus 100, represent characteristic features.

Because of the features, the X-ray CT apparatus 100 according to the first embodiment is configured to be capable to perform a scan with an X-ray dose optimal for each subject by automatically controlling the start/end of scanning plans during the scan in accordance with the density of a contrast medium.

Specifically, the X-ray CT apparatus 100 according to the first embodiment is configured such that the system control unit 38 detects index values indicating a contrast medium density in an ROI set on an image reconstructed during a scan, creates a curve indicating temporal variations in the contrast medium density in the ROI based on the detected index values, detects switch timing of scanning plans based on a gradient of the curve, and skips the rest of a scanning plan in execution and starts the next scanning plan upon detecting the switch timing. A configuration of the system control unit 38 and a process procedure performed by the system control unit 38 are explained below in detail.

Figure 2:
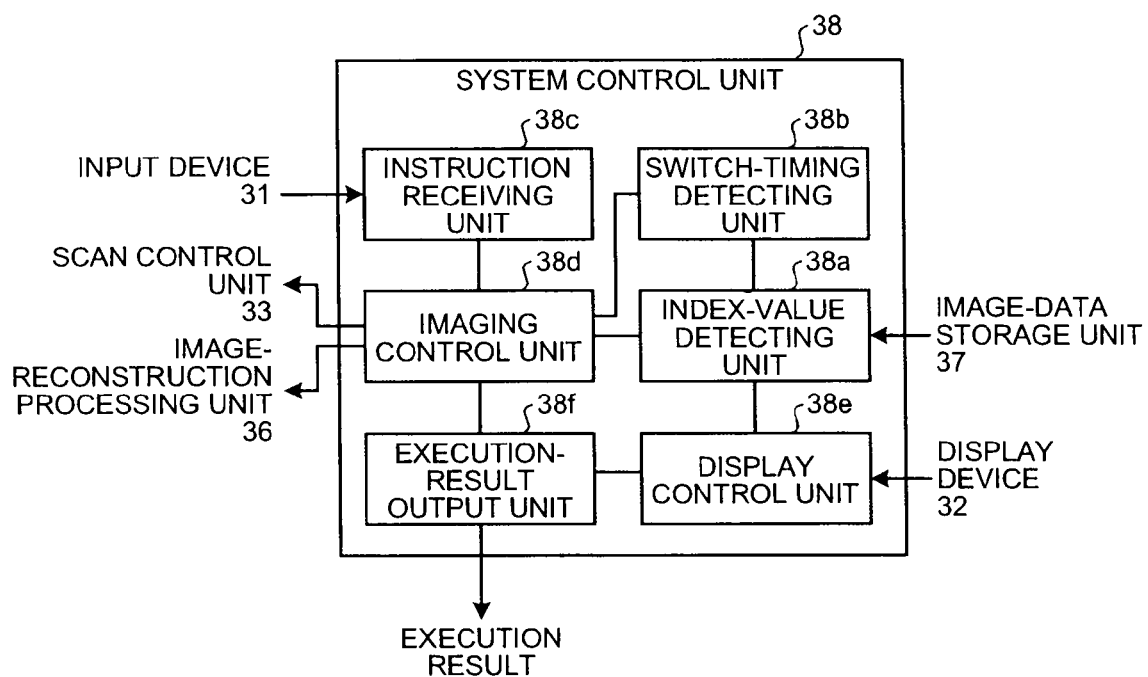
FIG. 2 is a functional block diagram of a configuration of a system control unit shown in FIG. 1.

At first, a configuration of the system control unit 38 is explained below. FIG. 2 is a functional block diagram of a configuration of the system control unit 38. As shown in FIG. 2, the system control unit 38 includes an index-value detecting unit 38a, a switch-timing detecting unit 38b, an instruction receiving unit 38c, an imaging control unit 38d, a display control unit 38e, and an execution-result output unit 38f.

The index-value detecting unit 38a detects an index value that indicates a contrast medium density in an ROI set on an image reconstructed during a scan. Although the first embodiment is explained below in a case of using a CT value as an index value indicating a contrast medium density, a value other than a CT value can be used as long as the value can indicate a contrast medium density.

Specifically, when the image-reconstruction processing unit 36 reconstructs image data, the index-value detecting unit 38a reads the reconstructed image data from the image-data storage unit 37 each time. Each time when reading the image data, the index-value detecting unit 38a detects a CT value in an ROI predetermined on each image data, and stores the detected CT value into, for example, a not-shown internal memory, temporally. It is assumed that the ROI that is a region in which the CT value is detected is set by the operator via the input device 31 before the scan.

The switch-timing detecting unit 38b creates a curve that indicates temporal variations in the contrast medium density in the ROI based on index values detected by the index-value detecting unit 38a, and detects switch timing of the scanning plan based on a gradient of the curve. The curve used herein indicates temporal variations in a contrast medium density and is hereinafter referred to as a Time Density Curve (TDC).

The first embodiment is explained below in a case where the switch-timing detecting unit 38b detects switch timing by detecting an inflection point that appears on a curve indicating temporal variations in the contrast medium density in the ROI based on a gradient of the curve.

Specifically, the switch-timing detecting unit 38b reads CT values detected by the index-value detecting unit 38a from the internal memory described above, creates a TDC based on the read CT values, and detects whether a predefined inflection point appears on the created TDC. For example, the switch-timing detecting unit 38b detects a "first inflection point" at which the rise in the contrast medium density peaks, and a "second inflection point" at which the decrease in the contrast medium density turns gradual.

A method of detecting such inflection points, various known methods can be used. For example, based on CT values temporally stored in the internal memory, a difference between a CT value detected at a previous time point and a CT value at the present time point is calculated sequentially one by one, and a point at which the difference turns from plus to minus, or minus to plus, is detected as an inflection point. Alternatively, preliminarily, the shape of a curve desired to detect is defined, and then an inflection point can be detected by comparing the defined curve and the shape of the created TDC (curve fitting). As described above, various methods can be used as a method of detecting an inflection point; however, it is desirable to employ a method by which the highest robustness is achieved.

The instruction receiving unit 38c receives various instructions related to switching of scanning plans from the operator. For example, the instruction receiving unit 38c receives from the operator via the input device 31, for example, an instruction to start a scan, or an instruction to skip the rest of a scanning plan in execution and to start the next scanning plan (hereinafter, "skip instruction"). When receiving an instruction, the instruction receiving unit 38c notifies the imaging control unit 38d, which will be described later, that the instruction is received.

The imaging control unit 38d controls the scan control unit 33 and the image-reconstruction processing unit 36 based on the sequential scanning plans, and switches scanning plans during a scan based on change in the contrast medium density in an ROI and an instruction from the operator. It is assumed that the scanning plans used in the scan are predetermined by the operator before the scan.

Specifically, when the instruction receiving unit 38c notifies that the instruction to start a scan is received, the imaging control unit 38d starts the scan based on the predetermined scanning plans. During a prep scan, the imaging control unit 38d controls the scan control unit 33 so as to start a main scan with timing when a CT value exceeds a threshold value.

According to the first embodiment, the imaging control unit 38d performs a dynamic scan as a main scan. The dynamic scan is a method of reconstructing a dynamic image of a scan subject portion of the subject P (for example, the brain or the heart) by repeatedly irradiating a region including the scan subject portion with X-rays. By performing the dynamic scan, a state of the contrast medium flowing through the scan subject portion can be observed.

The dynamic scan can be performed by simultaneously detecting X-rays that have passed through the region including the scan subject portion by using the FPD of multiple arrays as the X-ray detector 13 as described in the first embodiment; moreover, the dynamic scan can be performed by repeatedly irradiating the region including the scan subject portion with X-rays in spiral, for example, by reciprocating the top plate 21 in the slice direction.

When the switch-timing detecting unit 38b detects an inflection point appearing on the TDC of the CT values while executing the main scan (during the scan), the imaging control unit 38d then controls the scan control unit 33 so as to skip the rest of a scanning plan in execution at the moment and to start the next scanning plan.

For example, it is assumed that scanning plans A, B, and C are sequentially set by the operator. In such case, when the switch-timing detecting unit 38b detects the first inflection point, the imaging control unit 38d controls the scan control unit 33 so as to skip the rest of the scanning plan A in execution at first, and then to start the next scanning plan B. After that, when the switch-timing detecting unit 38b detects the second inflection point, the imaging control unit 38d controls the scan control unit 33 so as to skip the rest of the scanning plan B in execution at the moment and to start the next scanning plan C.

On the other hand, also when the instruction receiving unit 38c notifies that a skip instruction is received during the scan, the imaging control unit 38d controls the scan control unit 33 so as to skip the rest of a scanning plan in execution at the moment and to start the next scanning plan. It can be configured such that if the imaging control unit 38d once switches the scanning plans in accordance with the skip instruction, after that, the imaging control unit 38d does not switch the scanning plans upon detecting an inflection point by the switch-timing detecting unit 38b.

Moreover, the imaging control unit 38d sequentially reads CT values detected by the index-value detecting unit 38a from the internal memory during the scan, and when the read CT value becomes below a termination threshold value; the imaging control unit 38d skips the rest of the scanning plan in execution at the moment, and terminates the scan. After controlling the scan control unit 33 so as to terminate the scan, the imaging control unit 38d instructs the execution-result output unit 38f, which will be described later, so as to output information about the TDC and the executed scanning plan.

The display control unit 38e displays during the scan a curve that indicates temporal variations in a contrast medium density in an ROI, and information about an executed scanning plan. Specifically, the display control unit 38e displays a TDC of CT values in an ROI onto the display device 32 based on CT values detected by the index-value detecting unit 38a, and further displays information about scanning plans in a setting stage that are set before the scan, and information about a scanning plan that is executed during the scan.

FIGS. 3 to 6 are schematic diagrams for explaining display of a TDC and scanning plans by the display control unit 38e, and each depict a case where the scanning plans A, B, and C are sequentially set.

Figure 3:
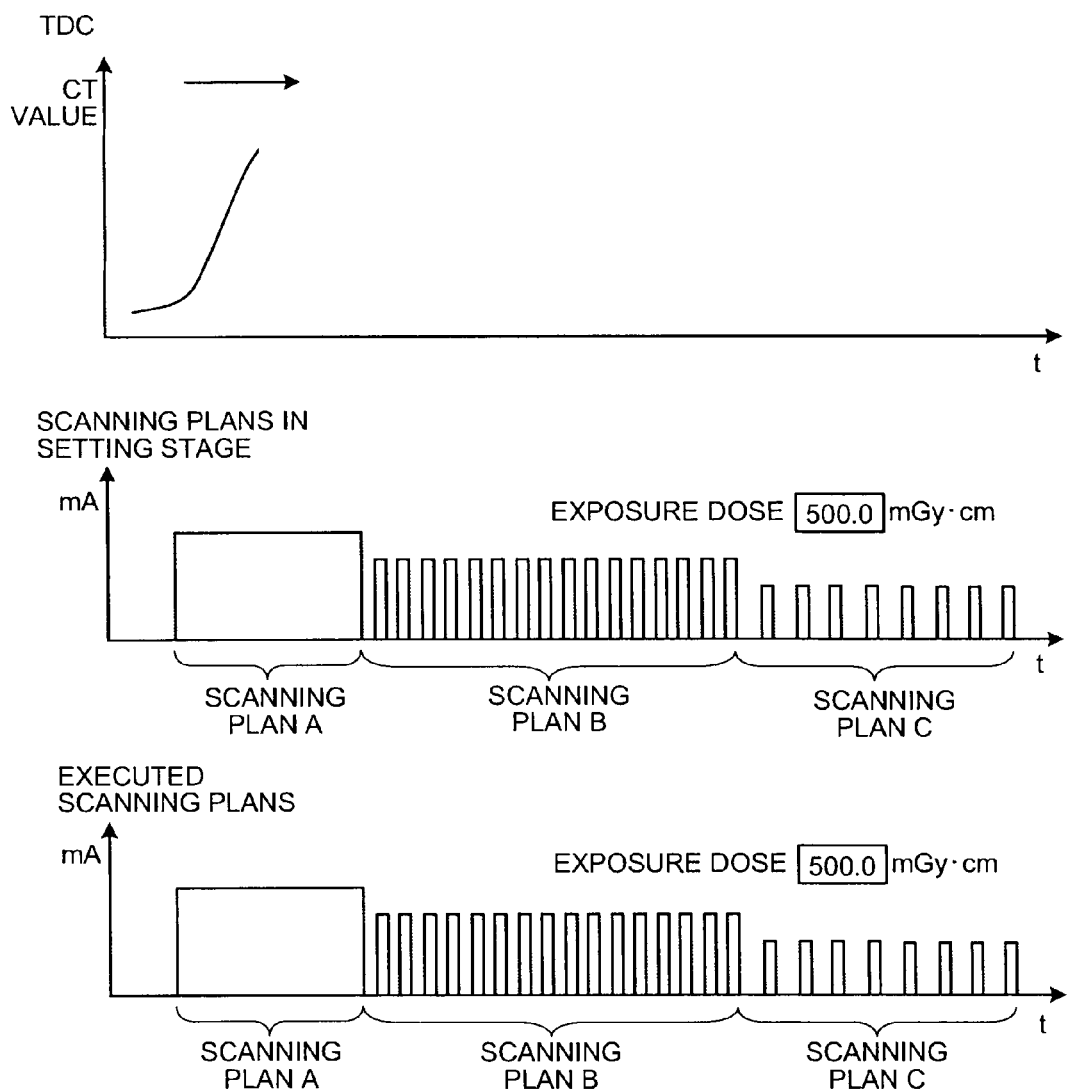
FIG. 3 is a schematic diagram (1) for explaining display of a Time Density Curve (TDC) and scanning plans by a display control unit shown in FIG. 1.

For example, as shown in FIG. 3, the display control unit 38e displays a TDC of CT values in the upper section, a schematic diagram that indicates scanning plans in the setting stage and an exposure dose according to the scanning plans in the middle section, and a schematic diagram that indicates executed scanning plans and an exposure dose resulted from the scanning plans in the lower section.

While displaying the information shown in the figure, the display control unit 38e displays the TDC so as to extend in the right direction in the figure as the scan proceeds, and displays the schematic diagram of the scanning plans in the setting stage as it is in the state displayed at the start of the scan without change until the termination of the scan. Moreover, when the scanning plan is switched during the scan, the display control unit 38e changes display of the schematic diagram indicating executed scanning plans and an exposure dose resulted from the scanning plans so as to depict the latest state of the scanning plans at the moment.

Figure 4:
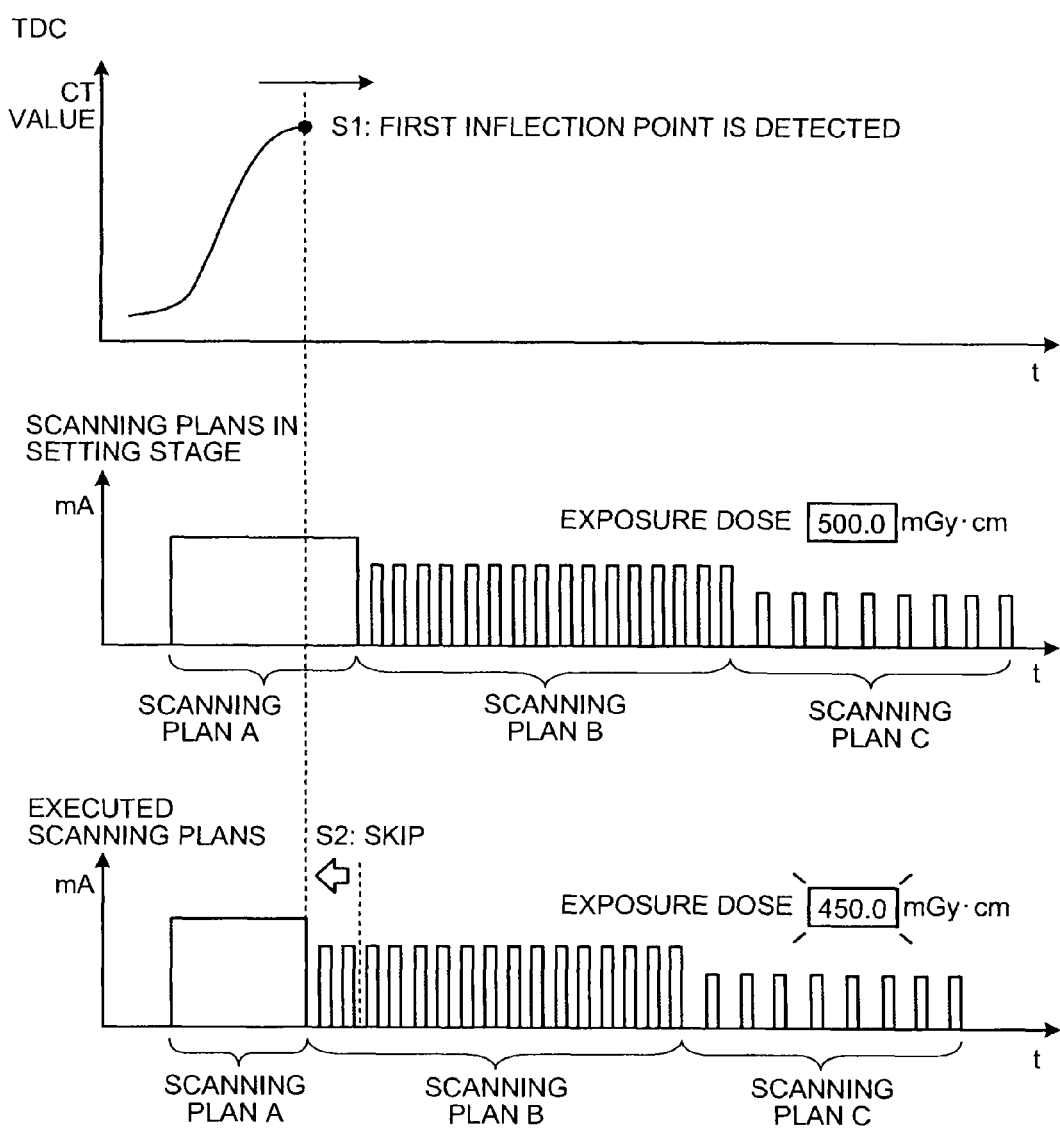
FIG. 4 is a schematic diagram (2) for explaining display of a TDC and scanning plans by the display control unit.

For example, as shown in FIG. 4, when the switch-timing detecting unit 38b detects the first inflection point (see S1 shown in FIG. 4), by synchronizing display with timing when the imaging control unit 38d skips the rest of the scanning plan A and starts the next scanning plan B, the display control unit 38e changes display of the executed scanning plans such that the scanning plan B starts from the timing, simultaneously recalculates an exposure dose based on the changed scanning plans, and displays the recalculated exposure dose (see S2 shown in FIG. 4).

Figure 5:
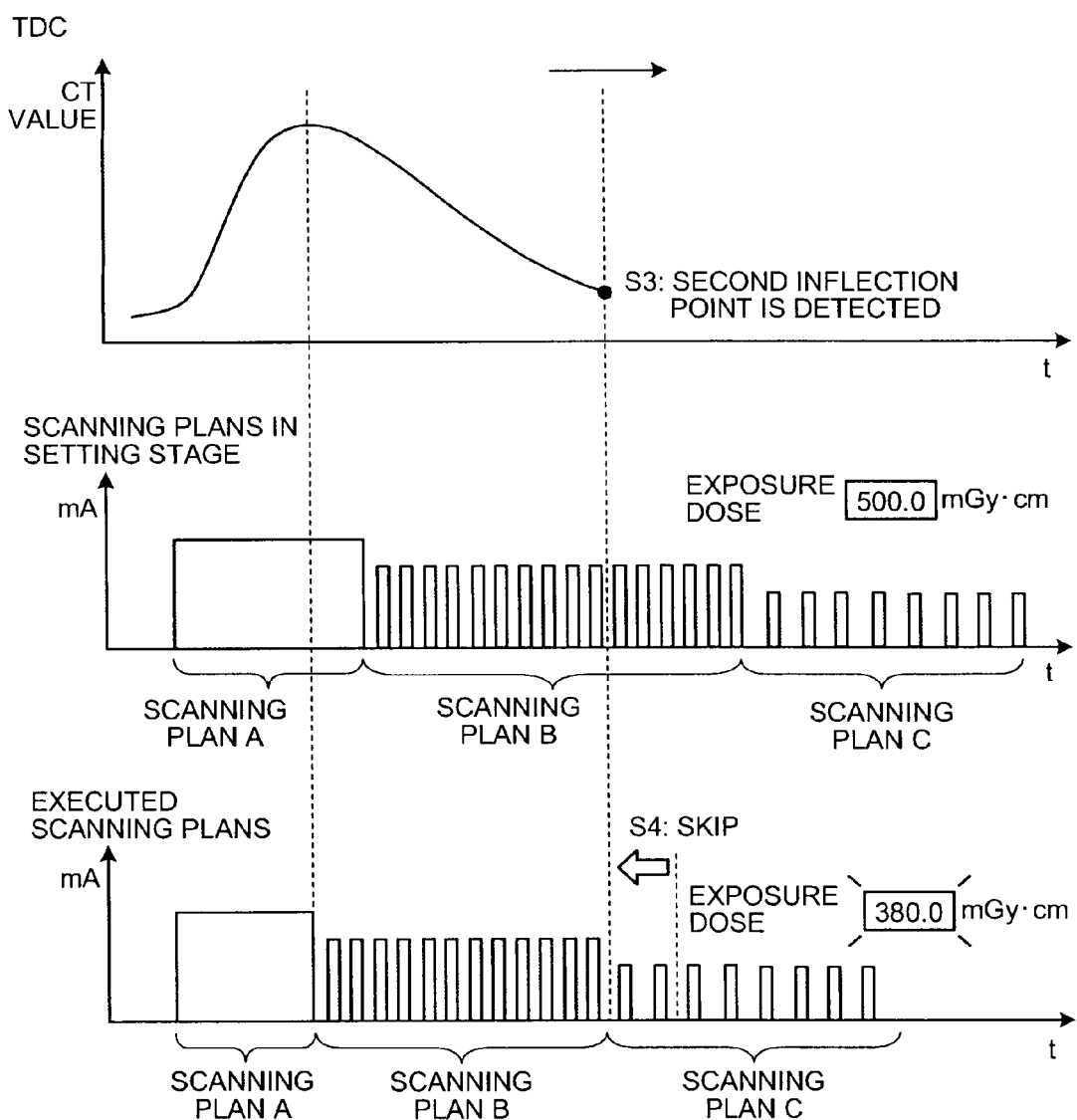
FIG. 5 is a schematic diagram (3) for explaining display of a TDC and scanning plans by the display control unit.

Subsequently, as shown in FIG. 5, when the switch-timing detecting unit 38b detects the second inflection point (see S3 shown in FIG. 5), by synchronizing display with timing when the imaging control unit 38d skips the rest of the scanning plan B and starts the next scanning plan C, the display control unit 38e changes display of the executed scanning plans such that the scanning plan C starts from the timing, simultaneously recalculates an exposure dose based on the changed scanning plans, and displays the recalculated exposure dose (see S4 shown in FIG. 5).

Figure 6:
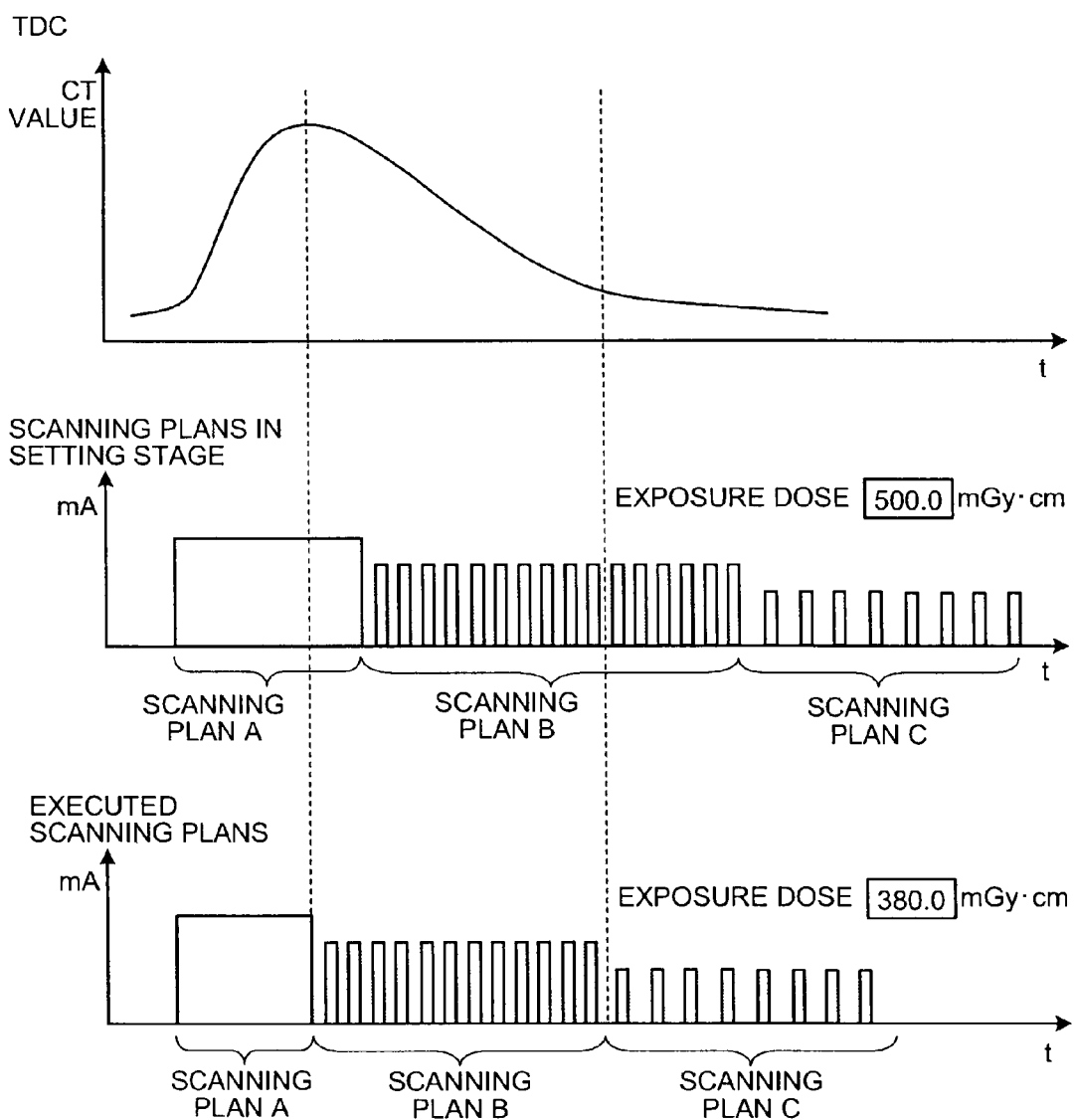
FIG. 6 is a schematic diagram (4) for explaining display of a TDC and scanning plans by the display control unit.

After the scan, as shown in FIG. 6, as well as a TDC that indicates temporal variations in CT values detected during the scan, the scanning plans set before the scan, and the scanning plans executed during the scan are displayed separately, and furthermore, an exposure dose according to the scanning plans set before the scan and an exposure dose resulted from the executed scanning plans are displayed, respectively.

In this way, even if individual scanning plans are set rather long before a scan, scanning plans can be switched by the imaging control unit 38d during the scan in accordance with change in CT values, so that an excessive irradiation with X-rays to a subject can be automatically avoided.

Moreover, because respective scanning plans and respective exposure doses before and after a scan are simultaneously displayed during the scan and after the scan, the operator can efficiently perform a review of the scanning plans in the setting stage and planning of scanning plans for subsequent scans.

The execution-result output unit 38f outputs information on a curve that indicates temporal variations in a contrast medium density and executed scanning plans that are displayed by the display control unit 38e, after the scan termination. Specifically, when the imaging control unit 38d instructs the execution-result output unit 38f to output a TDC and an execution result of scanning plans, the execution-result output unit 38f outputs an execution result that depicts information, for example, information on the TDC, the scanning plans in the setting stage, and the executed scanning plans as shown in FIG. 6, to an output device, such as a printer (not shown).

The execution-result output unit 38f can be configured to store, for example, an output execution result, into a certain storage unit for each subject. Accordingly, the operator can output the execution result again with desired timing after the scan.

Figure 7:
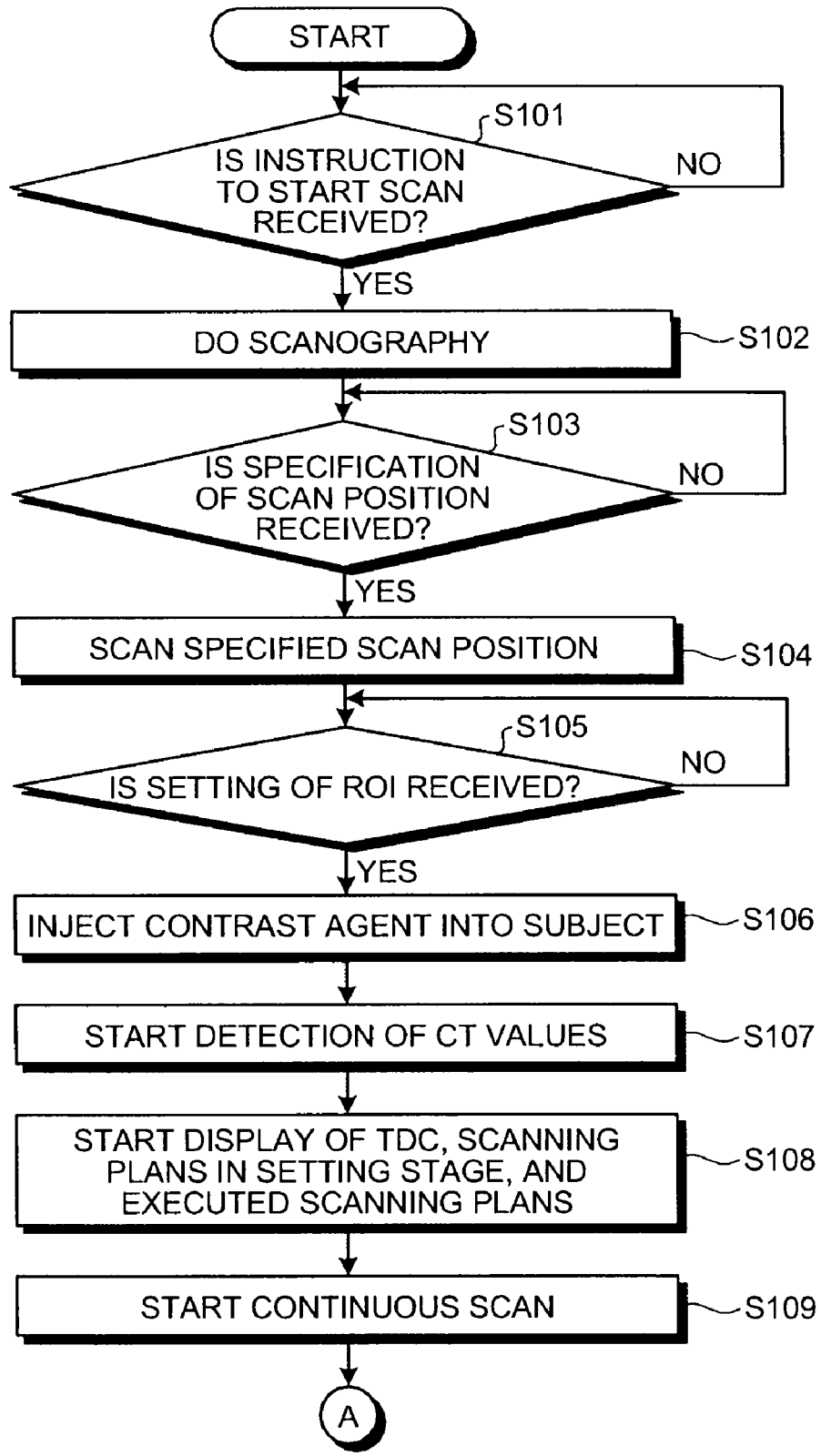
FIG. 7 is a flowchart (1) of a process procedure performed by the X-ray CT apparatus according to the first embodiment.
Figure 8:
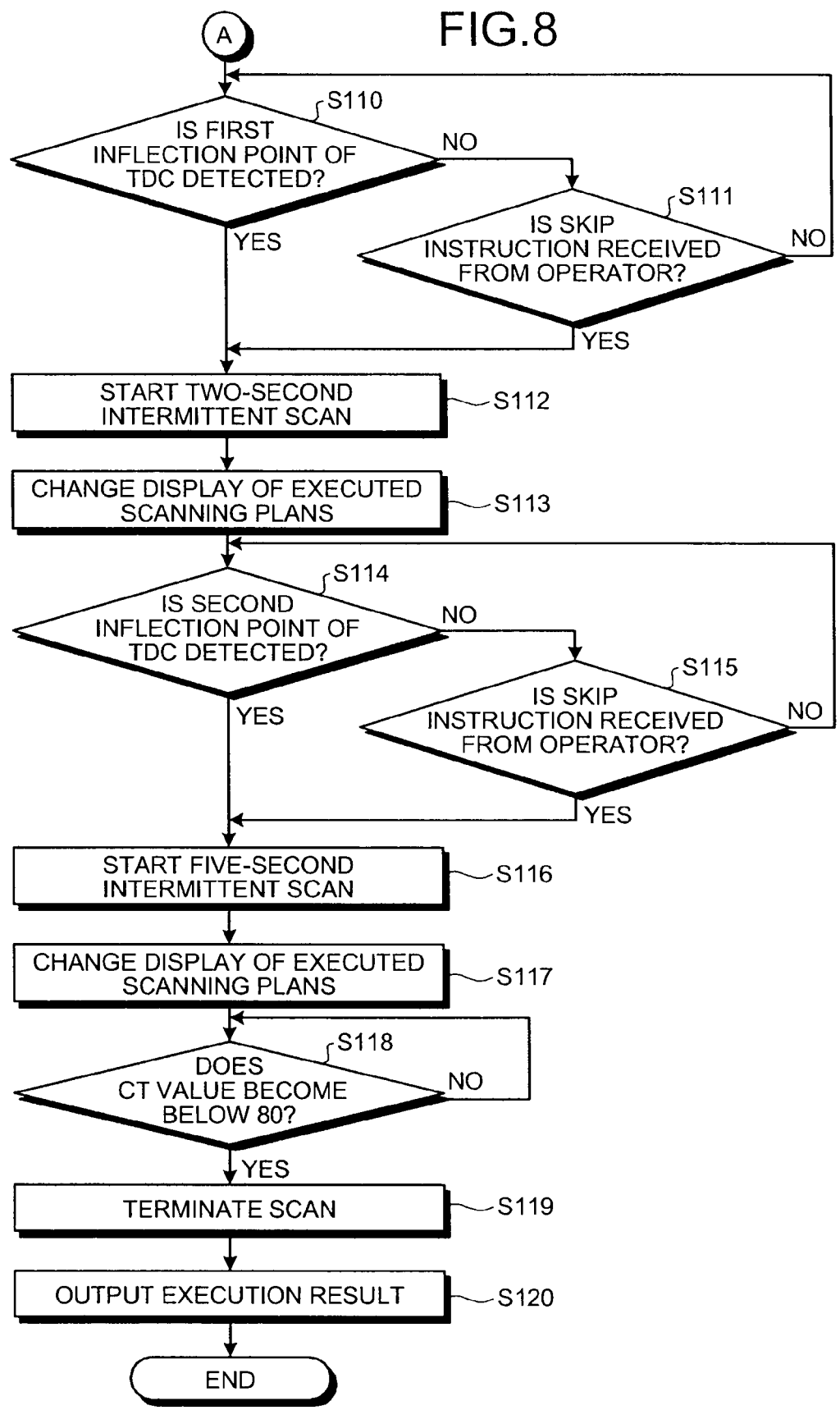
FIG. 8 is a flowchart (2) of the process procedure performed by the X-ray CT apparatus according to the first embodiment.

A process procedure performed by the X-ray CT apparatus 100 according to the first embodiment is explained below. FIGS. 7 and 8 are flowcharts of a process procedure performed by the X-ray CT apparatus 100 according to the first embodiment. Processing performed by the system control unit 38 is mainly explained below.

It is assumed in a case explained below as an example that scanning plans, namely, (1) scanography scanning, (2) Scan & View (S & V), (3) continuous scan (20 seconds), (4) two-second intermittent scan (30 seconds), and (5) five-second intermittent scan (30 seconds) are already set in this order, and a threshold value of CT values to be used for determination of a scan termination is 80.

The continuous scan is a plan of continuous irradiation with X-rays, the two-second intermittent scan is a plan of intermittent irradiation with X-rays with two-second intervals, and the five-second intermittent scan is a plan of intermittent irradiation with X-rays with five-second intervals.

In this case, according to the system control unit 38 of the X-ray CT apparatus 100 of the first embodiment, as shown in FIG. 7, when the instruction receiving unit 38c receives an instruction to start a scan from an operator (Yes at Step S101), the imaging control unit 38d controls the scan control unit 33 so as to do scanography (Step S102).

When the instruction receiving unit 38c receives a specification of a scan position on the scanography from the operator (Yes at Step S103), the imaging control unit 38d controls the scan control unit 33 so that the specified scan position is scanned (Step S104).

Subsequently, when the instruction receiving unit 38c receives setting of an ROI on image data that is taken by the scan (Yes at Step S105), a contrast medium is injected into the subject as the imaging control unit 38d performs, for example, injector synchronization (Step S106), and then the index-value detecting unit 38a starts to detect CT values (Step S107).

The display control unit 38e then starts displaying a TDC, scanning plans in the setting stage, and executed scanning plans (Step S108), and the imaging control unit 38d starts a continuous scan by controlling the scan control unit 33 (Step S109).

Subsequently, as shown in FIG. 8, when the switch-timing detecting unit 38b detects the first inflection point of the TDC (Yes at Step S110), or when the instruction receiving unit 38c receives a skip instruction from the operator (Yes at Step S111), the imaging control unit 38d starts a two-second intermittent scan by controlling the scan control unit 33 (Step S112), and the display control unit 38e changes display of the executed scanning plans (Step S113).

After that, when the switch-timing detecting unit 38b detects the second inflection point of the TDC (Yes at Step S114), or when the instruction receiving unit 38c receives a skip instruction from the operator (Yes at Step S115), the imaging control unit 38d starts a five-second intermittent scan by controlling the scan control unit 33 (Step S116), and the display control unit 38e changes display of the executed scanning plans (Step S117).

After that, when a CT value becomes below 80 (Yes at Step S118), the imaging control unit 38d terminates the scan by controlling the scan control unit 33 (Step S119), and the execution-result output unit 38f outputs an execution result that includes information on the TDC, the scanning plans in the setting stage, and the executed scanning plans (Step S120).

As described above, according to the first embodiment, in the system control unit 38 that performs overall control of the X-ray CT apparatus 100, the index-value detecting unit 38a detects an index value indicating a contrast medium density in an ROI that is set on an image reconstructed during a scan; the switch-timing detecting unit 38b detects an inflection point appearing on a curve that indicates temporal variations in the contrast medium density in the ROI based on the index value detected by the index-value detecting unit 38a; and when the switch-timing detecting unit 38b detects an inflection point, the imaging control unit 38d performs control so as to skip the rest of a scanning plan in execution and to start the next scanning plan. Accordingly the start/end of a scanning plan can be automatically controlled during a scan in accordance with the density of a contrast medium, so that the scan can be performed with an X-ray dose optimal for each subject.

Moreover, according to the first embodiment, the instruction receiving unit 38c receives an instruction to skip the rest of a scanning plan in execution and to start the next scanning plan from the operator; when the instruction receiving unit 38c receives the instruction about switching of scanning plans, the imaging control unit 38d performs control so as to skip the rest of the scanning plan in execution and to start the next scanning plan. Accordingly, not only waiting the scanning plans being automatically switched, but also the operator can switch the scanning plans with arbitrary timing.

Furthermore, according to the first embodiment, when an index value detected by the index-value detecting unit 38a becomes below a termination threshold value, the imaging control unit 38d performs control so as to skip the rest of a scanning plan in execution at the moment and terminate the scan. Accordingly, when the density of a contrast medium becomes lower than an adequate level for a scan, the scan can be automatically terminated, thereby avoiding needlessly lingering the scan, and preventing the subject from being irradiated with excessive X-rays.

Moreover, according to the first embodiment, the display control unit 38e displays during a scan a curve that indicates temporal variations in a contrast medium density in an ROI based on index values detected by the index-value detecting unit 38a. Accordingly, the operator can easily grasp variations in the density of the contrast medium, and consequently can determine timing of switching scanning plans with arbitrary timing.

Furthermore, according to the first embodiment, the display control unit 38e displays information on executed scanning plans during a scan, so that the operator can easily grasp a scanning plan in execution and executed scanning plans.

Moreover, according to the first embodiment, the execution-result output unit 38f outputs information on a curve that indicates temporal variations in a contrast medium density and executed scanning plans that are displayed by the display control unit 38e, after the scan termination. Accordingly, when the same subject is scanned in a next occasion, the output information can be used as reference information for setting of scanning plans, so that scanning plans optimal for each subject can be set.

Although the first embodiment according to the present invention has been explained above, the present invention can be implemented in different forms in addition to the first embodiment described above. Another embodiment included in the present invention is explained below as a second embodiment.

(1) Control of Tube Current in Accordance with Standard Deviation (SD) Value

The first embodiment is explained above in a case where a scanning plan in execution is switched based on temporal variations in CT values in an ROI, however, the present invention is not limited to this. It can be configured such that, for example, the quality of a reconstructed image can be kept constant by allowing an operator to set another ROI and a reference value of a standard deviation (SD) value in an region in which a noise level is desired to be kept constant, detecting an SD value in the set ROI, and performing control a dose of X-ray such that the detected SD value is to be kept at the reference value. The SD value here means a standard deviation of noises in a reconstructed image.

In such case, specifically, the index-value detecting unit 38a further detects an SD value in another ROI set on an image reconstructed during a scan, and the imaging control unit 38d changes the amount of a tube current generating X-rays with respect to each scanning plan such that the SD value detected by the index-value detecting unit 38a is to be kept at a certain reference value.

Generally, when an SD value is large, the quality of an image is low; by contrast, when an SD value is small, the quality of an image is high. For this reason, when an SD value is larger than the reference value, the imaging control unit 38d increases a dose of X-ray irradiation by increasing a tube current; by contrast, when an SD value is smaller than the reference value, the imaging control unit 38d reduces a dose of X-ray irradiation by decreasing a tube current. In this way, the imaging control unit 38d automatically adjusts the amount of a tube current in accordance with an SD value, so that the quality of a reconstructed image can be kept constant.

(2) Automatic Extension of Scanning Plan

The first embodiment is explained in a case where the imaging control unit 38d performs control so as to skip the rest of a scanning plan in execution and to start the next scanning plan upon detecting an inflection point by the switch-timing detecting unit 38b, however, the present invention is not limited to this. It can be configured such that, for example, if any inflection point has not been detected yet meanwhile a scan time of a scanning plan in execution has expired, the scanning plan is extended until an inflection point is detected.

Figure 9:
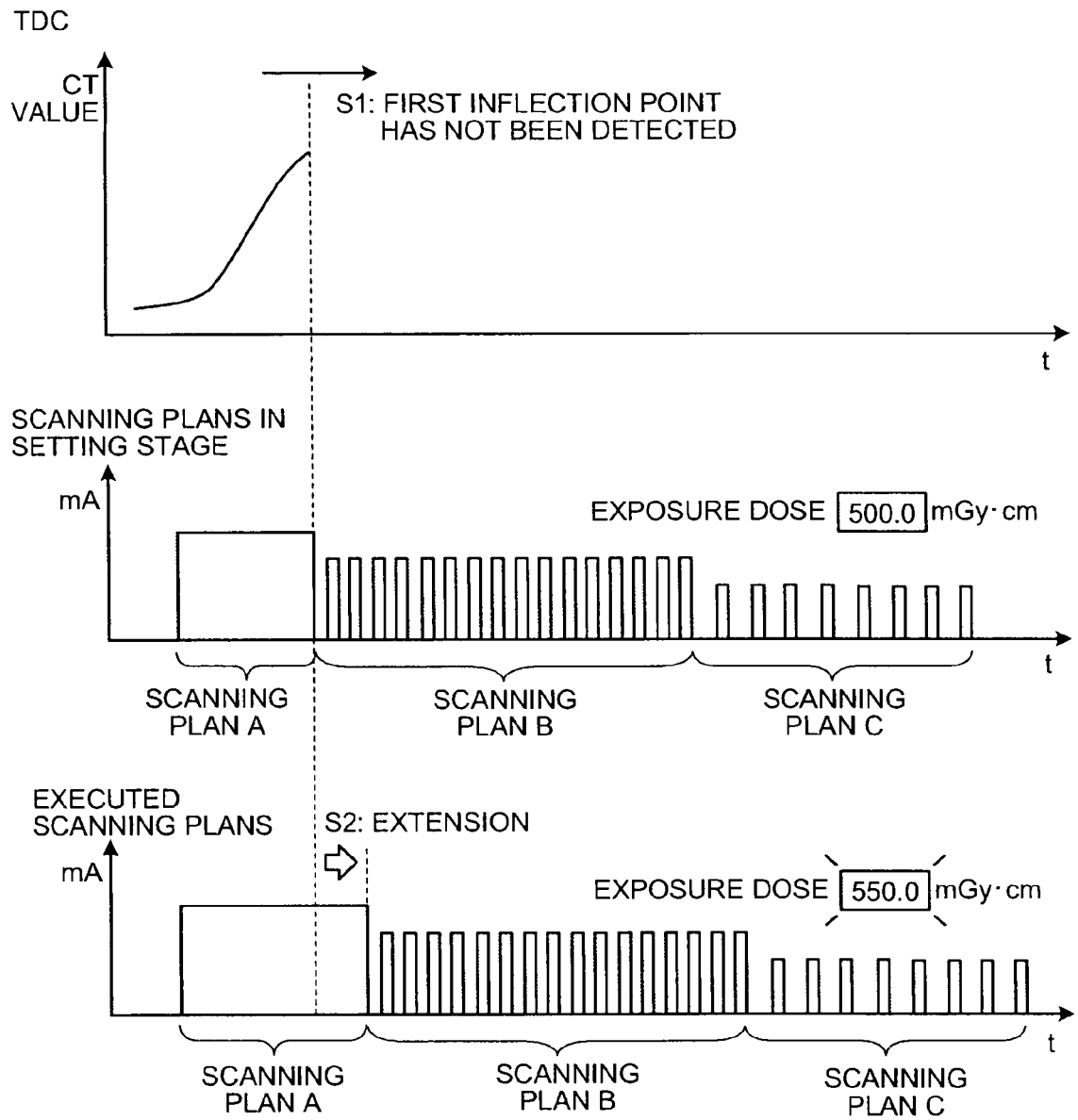
FIG. 9 is a schematic diagram for explaining a case where a scanning plan is automatically extended according to a second embodiment of the present invention.

FIG. 9 is a schematic diagram for explaining a case where a scanning plan is automatically extended. As shown in FIG. 9, in such case, specifically, if the switch-timing detecting unit 38b has not detected any inflection point yet, meanwhile a scan time of a scanning plan in execution has expired (see S1 shown in FIG. 9); the imaging control unit 38d controls the scan control unit 33 so as to extend the scanning plan until an inflection point is detected (see S2 shown in FIG. 9).

Moreover, in such case, the instruction receiving unit 38c further receives an instruction to extend the scanning plan in execution from the operator. When the instruction receiving unit 38c receives the instruction to extend the scanning plan, the imaging control unit 38d controls the scan control unit 33 so as to extend the scanning plan in execution.

In this way, the imaging control unit 38d performs control so as to extend a scanning plan based on a scan time of the scanning plan or an instruction from the operator, thereby extending the scan time automatically in accordance with an index value in an ROI even if the scan time is set short in the setting stage of the scanning plan, and resulting in that the scan can be performed with an X-ray dose optimal for each subject.

(3) Display of a Plurality of Curves

The first embodiment is explained above in a case where the display control unit 38e displays a single curve that indicates temporal variations in index values indicating the density of a contrast medium, however, the present invention is not limited to this. It can be configured to display a plurality of curves when a plurality of ROIs is set.

FIG. 10 is a schematic diagram for explaining a case of displaying a plurality of curves. As shown in FIG. 10, in such case, specifically, if a plurality of ROIs is set on an image, the display control unit 38e displays on the display device 32 a plurality of TDCs that indicates temporal variations in contrast medium densities in respective ROIs (see C1 and C2 shown in FIG. 10).

In this way, as the display control unit 38e displays curves about respective ROIs that indicate temporal variations in index values indicating the densities of the contrast medium in ROIs, the operator can determine timing of switching the scanning plans with arbitrary timing as required while grasping variations in the densities of the contrast medium in a plurality of regions.

(4) Determination of Scan Termination According to Maximum Scan Time

The first embodiment described above is explained in a case where the imaging control unit 38d terminates a scan when a CT value detected by the index-value detecting unit 38a becomes below a termination threshold value, however, the present invention is not limited this. For example, it can be configured such that the imaging control unit 38d cumulates a total scan time from the start of a scan during the scan, and when the cumulative total scan time reaches a predetermined maximum scan time, the imaging control unit 38d controls the scan control unit 33 so as to skip the rest of a scanning plan in execution at the moment and to terminate the scan.

Accordingly, as the maximum scan time is set in advance by taking into account an exposure dose to a subject, the scan is automatically terminated, thereby avoiding needlessly irradiating the subject with X-rays.

The components of each device shown in the drawings in the above embodiments are conceptual for describing functions, and not necessarily to be physically configured as shown in the drawings. In other words, concrete forms of distribution and integration of the units are not limited to those shown in the drawings, and all or part of the units can be configured to be functionally or physically distributed and integrated in arbitrary units depending on various loads and conditions of the use.

As described above, the X-ray CT apparatus and the tomography method according to the embodiments of the present invention are useful when taking a four-dimensional image that one temporal dimension is added to three spatial dimensions, and suitable particularly when performing a scan by irradiating a subject with X-rays continuously or intermittently based on a plurality of sequential scanning plans.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
an imaging unit configured to irradiate a subject, switching scanning conditions, with X-rays continuously or intermittently, and to reconstruct an image by detecting X-rays passed through the subject;
an index-value detecting unit configured to detect an index value that indicates a contrast medium density in the image reconstructed by the imaging unit during a scan;
a switch-timing detecting unit configured to detect switch timing of the scanning conditions based on the index value detected by the index-value detecting unit; and
an imaging control unit configured to control the imaging unit so as to perform a prep scan and a main scan, the main scan including a first scan with a first scanning condition and a second scan with a second scanning condition; wherein
the imaging control unit controls, during the prep scan, the imaging unit so as to start the main scan with a timing when the index value exceeds a threshold value, and controls, during the main scan, the imaging unit so as to skip a rest of the first scan in execution and to start the second scan upon detecting the switch timing by the switch-timing detecting unit.

2. The apparatus according to claim 1, wherein the imaging unit performs as the main scan a dynamic scan through which as the image a dynamic image of a scan subject portion of the subject is reconstructed by repeatedly irradiating a region including the scan subject portion with X-rays.

3. The apparatus according to claim 2, wherein the imaging unit detects X-rays with a Flat Panel Detector of multiple arrays that simultaneously detects X-rays passed through the region including the scan subject portion.

4. The apparatus according to claim 1, wherein the switch-timing detecting unit creates a curve that indicates temporal variations in the contrast medium density based on the index value, and detects the switch timing based on a gradient of the created curve.

5. The apparatus according to claim 4, wherein
the index-value detecting unit detects as the index value an index value that indicates the contrast medium density in a region of interest set on the image reconstructed by the imaging unit, and
the switch-timing detecting unit creates as the curve a curve that indicates the temporal variations in the contrast medium density in the region of interest.

6. The apparatus according to claim 4, wherein the switch-timing detecting unit detects the switch timing by detecting an inflection point that appears on the curve based on a gradient of the curve.

7. The apparatus according to claim 1, wherein the imaging control unit controls the imaging unit so as to skip the rest of the main scan currently in execution and to terminate scanning, when the index value detected by the index-value detecting unit becomes below a termination threshold value.

8. The apparatus according to claim 1, wherein the imaging control unit controls the imaging unit so as to skip the rest of the main scan currently in execution and to terminate scanning, when a total scan time from a start of the main scan reaches a predetermined maximum scan time.

9. The apparatus according to claim 1, further comprising a display control unit configured to display during the main scan a curve that indicates temporal variations in the contrast medium density based on the index value detected by the index-value detecting unit.

10. An X-ray CT apparatus comprising:
an imaging unit configured to irradiate a subject, switching scanning conditions, with X-rays continuously or intermittently, and to reconstruct an image by detecting X-rays passed through the subject;
an index-value detecting unit configured to detect an index value that indicates a contrast medium density in the image reconstructed by the imaging unit during a scan;
an imaging control unit configured to control the imaging unit so as to perform a prep scan and a main scan, and control, during the prep scan, the imaging unit so as to start the main scan with a timing when the index value exceeds a threshold value; and
a display control unit configured to display during the main scan a curve that indicates temporal variations in the contrast medium density based on the index value detected by the index-value detecting unit.

11. The apparatus according to claim 10, further comprising:
an instruction receiving unit configured to receive from an operator an instruction to skip a rest of a first scan with a first scanning condition in execution and to start a second scan with a second scanning condition, the first scan and the second scan being included in the main scan; and
an imaging control unit configured to control the imaging unit so as to skip the rest of the first scan with the first scanning condition and to start the second scan with the second scanning condition upon receiving the instruction by the instruction receiving unit.

12. The apparatus according to claim 10, wherein
the index-value detecting unit detects as the index value an index value that indicates the contrast medium density in a region of interest set on the image reconstructed by the imaging unit, and
the display control unit displays during the main scan as the curve a curve that indicates the temporal variations in the contrast medium density in the region of interest.

13. The apparatus according to claim 12, wherein the display control unit displays as the curve a plurality of curves that indicates temporal variations in contrast medium densities in respective of a plurality of regions of interest, when as the region of interest the plurality of regions of interest are set on the image reconstructed by the imaging unit.

14. The apparatus according to claim 10, wherein the display control unit further displays information about executed scans during the main scan.

15. A tomography method comprising:
irradiating a subject, switching scanning conditions, with X-rays continuously or intermittently, and reconstructing an image by detecting X-rays passed through the subject, by an imaging unit;
detecting by an index-value detecting unit an index value that indicates a contrast medium density in the image reconstructed by the imaging unit during a scan;
detecting by a switch-timing detecting unit switch timing of the scanning conditions based on the index value detected by the index-value detecting unit; and
controlling the imaging unit by an imaging control unit so as to perform a prep scan and a main scan, the main scan including a first scan with a first scanning condition and a second scan with a second scanning condition; wherein
the imaging control unit controls, during the prep scan, the imaging unit so as to start the main scan with a timing when the index value exceeds a threshold value, and controls, during the main scan, the imaging unit so as to skip a rest of the first scan in execution and to start the second scan upon detecting the switch timing by the switch-timing detecting unit.

16. The method according to claim 15, wherein the imaging unit performs as the main scan a dynamic scan through which as the image a dynamic image of a scan subject portion of the subject is reconstructed by repeatedly irradiating a region including the scan subject portion with X-rays.

17. The method according to claim 16, wherein the imaging unit detects X-rays with a Flat Panel detector of multiple arrays that simultaneously detects X-rays passed through the region including the scan subject portion.

18. The method according to claim 15, wherein the switch-timing detecting unit creates a curve that indicates temporal variations in the contrast medium density based on the index value, and detects the switch timing based on a gradient of the created curve.

19. The method according to claim 18, wherein
the index-value detecting unit detects as the index value an index value that indicates the contrast medium density in a region of interest set on the image reconstructed by the imaging unit, and the switch-timing detecting unit creates as the curve a curve that indicates the temporal variations in the contrast medium density in the region of interest.

20. The method according to claim 18, wherein the switch-timing detecting unit detects the switch timing by detecting an inflection point that appears on the curve based on a gradient of the curve.

21. The method according to claim 15, wherein the imaging control unit controls the imaging unit so as to skip the rest of the main scan currently in execution and to terminate scanning, when the index value detected by the index-value detecting unit becomes below a termination threshold value.

22. The method according to claim 15, wherein the imaging control unit controls the imaging unit so as to skip the rest of the main scan currently in execution and to terminate scanning, when a total scan time from a start of the main scan reaches a predetermined maximum scan time.

23. The method according to claim 15, further comprising displaying by a display control unit during the main scan a curve that indicates temporal variations in the contrast medium density based on the index value detected by the index-value detecting unit.

24. A tomography method comprising:
irradiating a subject, switching scanning conditions, with X-rays continuously or intermittently, and reconstructing an image by detecting X-rays passed through the subject, by an imaging unit;
detecting by an index-value detecting unit an index value that indicates a contrast medium density in the image reconstructed by the imaging unit during a scan;
controlling the imaging unit by an imaging control unit so as to perform a prep scan and a main scan, and controlling, during the prep scan, the imaging unit by the imaging control unit so as to start the main scan with a timing when the index value exceeds a threshold value, and
displaying by a display control unit during the main scan a curve that indicates temporal variations in the contrast medium density based on the index value detected by the index-value detecting unit.

25. The method according to claim 24, further comprising:
receiving by an instruction receiving unit from an operator an instruction to skip a rest of a first scan with a first scanning condition in execution and to start a second scan with a second scanning condition, the first scan and the second scan being included in the main scan; and
controlling the imaging unit by an imaging control unit so as to skip the rest of the first scan with the first scanning condition and to start the second scan with the second scanning condition upon receiving the instruction by the instruction receiving unit.

26. The method according to claim 25, wherein
the index-value detecting unit detects as the index value an index value that indicates a contrast medium density in a region of interest set on the image reconstructed by the imaging unit, and
the display control unit displays during the main scan as the curve a curve that indicates the temporal variations in the contrast medium density in the region of interest.

27. The method according to claim 24, wherein the display control unit displays as the curve a plurality of curves that indicates temporal variations in contrast medium densities in of a plurality of respective regions of interest, when as the region of interest the plurality of regions of interest are set on the image reconstructed by the imaging unit.

28. The method according to claim 24, wherein the display control unit further displays information about executed scans during the main scan.

* * * * *